(12) United States Patent
Mori et al.

(10) Patent No.: US 10,151,916 B2
(45) Date of Patent: Dec. 11, 2018

(54) OPTICAL SCANNING OBSERVATION APPARATUS

(71) Applicant: OLYMPUS CORPORATION, Tokyo (JP)

(72) Inventors: Takeshi Mori, Tokyo (JP); Ken Fujinuma, Tokyo (JP)

(73) Assignee: Olympus Corporation, Tokyo (JP)

( * ) Notice: Subject to any disclaimer, the term of this patent is extended or adjusted under 35 U.S.C. 154(b) by 188 days.

(21) Appl. No.: 15/215,626

(22) Filed: Jul. 21, 2016

(65) Prior Publication Data

US 2016/0327782 A1 Nov. 10, 2016

Related U.S. Application Data

(63) Continuation of application No. PCT/JP2015/000302, filed on Jan. 23, 2015.

(30) Foreign Application Priority Data

Jan. 24, 2014 (JP) .................................. 2014-011413

(51) Int. Cl.
*G02B 23/24* (2006.01)
*A61B 1/00* (2006.01)
(Continued)

(52) U.S. Cl.
CPC ...... *G02B 23/2484* (2013.01); *A61B 1/00006* (2013.01); *A61B 1/00057* (2013.01); *A61B 1/00172* (2013.01); *A61B 1/07* (2013.01); *G02B 23/2469* (2013.01); *G02B 26/103* (2013.01); *H04N 5/2256* (2013.01); *H04N 5/2354* (2013.01); *H04N 2005/2255* (2013.01)

(58) Field of Classification Search
None
See application file for complete search history.

(56) References Cited

U.S. PATENT DOCUMENTS 7,436,564 B2 * 10/2008 Gomi .................. G02B 26/105
250/234
2002/0188176 A1 12/2002 Kuranishi
(Continued)

FOREIGN PATENT DOCUMENTS

| CN | 101449958 A | 6/2009 |
|----|-------------|--------|
| JP | 2002-360510 A | 12/2002 |

(Continued)

OTHER PUBLICATIONS

Chinese Office Action dated Jun. 2, 2017 in Chinese Patent Application No. 201580005031.9.
(Continued)

*Primary Examiner* — Jennifer D. Carruth
(74) *Attorney, Agent, or Firm* — Scully, Scott, Murphy & Presser, P.C.

(57) ABSTRACT

An optical scanning observation apparatus includes a light emission timing controller, a fiber, a driver, a photodetector, an offset processor that corrects an offset value based on an electrical signal output by the photodetector while a light emission timing controller suspends light emission of a light source, and a signal processor that generates an image signal based on the electrical signal for which the offset value was corrected by the offset processor.

8 Claims, 10 Drawing Sheets

(51) Int. Cl.
*G02B 26/10* (2006.01)
*A61B 1/07* (2006.01)
*H04N 5/225* (2006.01)
*H04N 5/235* (2006.01)

(56) References Cited

U.S. PATENT DOCUMENTS

2005/0020926 A1* 1/2005 Wiklof ............... A61B 1/00193
                                                        600/476
2011/0015528 A1   1/2011 Kobayashi

FOREIGN PATENT DOCUMENTS

| JP | 2005-234500 A | 9/2005 |
| JP | 2010-042128 A | 2/2010 |
| JP | 2011-019706 A | 2/2011 |
| JP | 2012-085715 A | 5/2012 |
| JP | 2013-178417 A | 9/2013 |
| JP | 2013-244045 A | 12/2013 |
| JP | 2014-69020 A | 4/2014 |

OTHER PUBLICATIONS

Japanese Office Action dated Aug. 29, 2017 in Japanese Patent Application No. 2014-011413.
International Search Report dated Apr. 21, 2015 issued in PCT/JP2015/000302.
Extended Supplementary European Search Report dated Nov. 17, 2017 received in 15740622.4.
Japanese Office Action dated Jun. 5, 2018 in Japanese Patent Application No. 2014-011413.

* cited by examiner

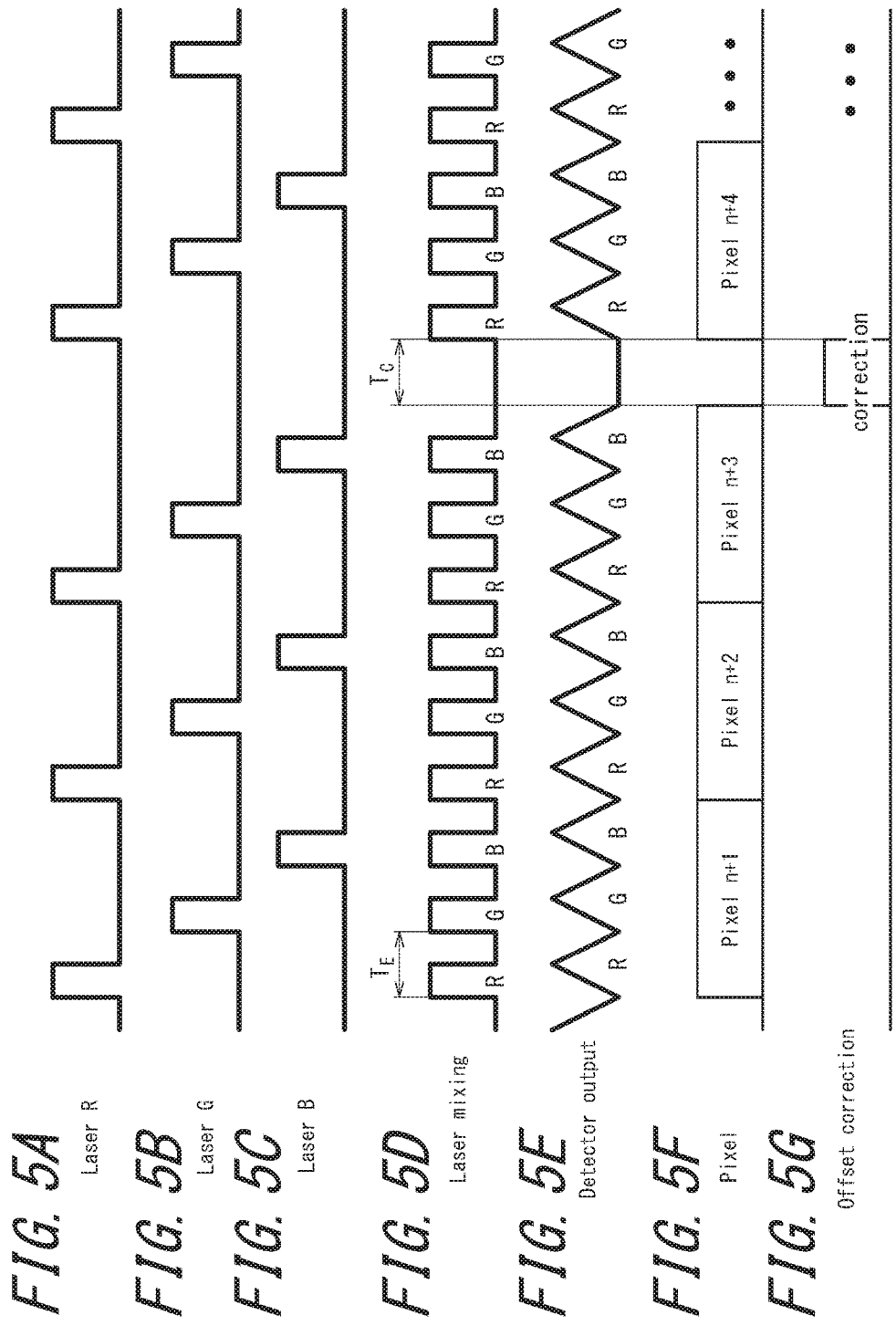

OPTICAL SCANNING OBSERVATION APPARATUS

CROSS-REFERENCE TO RELATED APPLICATION

The present application is a Continuing Application based on International Application PCT/JP2015/000302 filed on Jan. 23, 2015, which in turn claims priority to Japanese Patent Application No. 2014-11413 filed on Jan. 24, 2014, the entire disclosure of these earlier applications being incorporated herein by reference.

TECHNICAL FIELD

This disclosure relates to an optical scanning observation apparatus that optically scans an object by vibrating an optical fiber.

BACKGROUND

A known medical probe for observing an object using pulsed light of various wavelengths that is irradiated from a light source includes optical guiding means for guiding pulsed light incident from the light source and for emitting the pulsed light onto the object and optical delay means for providing a predetermined delay time that differs for each wavelength to reflected pulsed light of the object that is irradiated by the emitted pulsed light, the medical probe outputting the pulsed light provided with the delay time to predetermined photodetector means (for example, see JP 2010-42128 A (PTL 1)).

CITATION LIST

Patent Literature

PTL 1: JP 2010-42128 A

SUMMARY

An optical scanning observation apparatus according to this disclosure is for scanning an object with illumination light from a light source and acquiring an image of the object, the optical scanning observation apparatus including:
a light emission timing controller configured to control a light emission timing of the light source;
a fiber configured to guide the illumination light from the light source and emit the illumination light toward the object from a tip of the fiber, the tip being supported to allow oscillation;
a driver configured to drive the tip of the fiber by vibration;
a photodetector configured to detect detection light obtained from the object and convert the detection light obtained from the object to an electrical signal;
an offset processor configured to correct an offset value based on the electrical signal output by the photodetector while the light emission timing controller suspends light emission of the light source; and
a signal processor configured to generate an image signal based on the electrical signal for which the offset value was corrected by the offset processor.

The driver may oscillate the tip of the fiber in a spiral shape.

The driver may oscillate the tip of the fiber in a Lissajous curve.

The light emission timing controller may suspend light emission of the light source, and the offset processor may correct the offset value, in an outer peripheral region of an image generated based on the image signal or outside a display period of the image.

The optical scanning observation apparatus may further include an offset processing determiner configured to determine whether correction of the offset value is feasible based on the electrical signal output by the photodetector while the light emission timing controller suspends light emission of the light source; and
the offset processor may correct the offset value when the offset processing determiner determines that correction of the offset value is feasible.

BRIEF DESCRIPTION OF THE DRAWINGS

In the accompanying drawings:

FIGS. 5A to 5G illustrate an example of the relationship between the light emission timing and the correction timing of the offset value;

FIG. 12A is a cross-sectional diagram of the tip of the scope, FIG. 12B is an enlarged perspective view of the driver in FIG. 12A, and FIG. 12C is a cross-sectional view along a plane perpendicular to the axis of the optical fiber, illustrating a portion including the coils for generation of a deflecting magnetic field and the permanent magnet in FIG. 12B.

DETAILED DESCRIPTION

Embodiments are described below with reference to the drawings.

Embodiment 1

Figure 1:
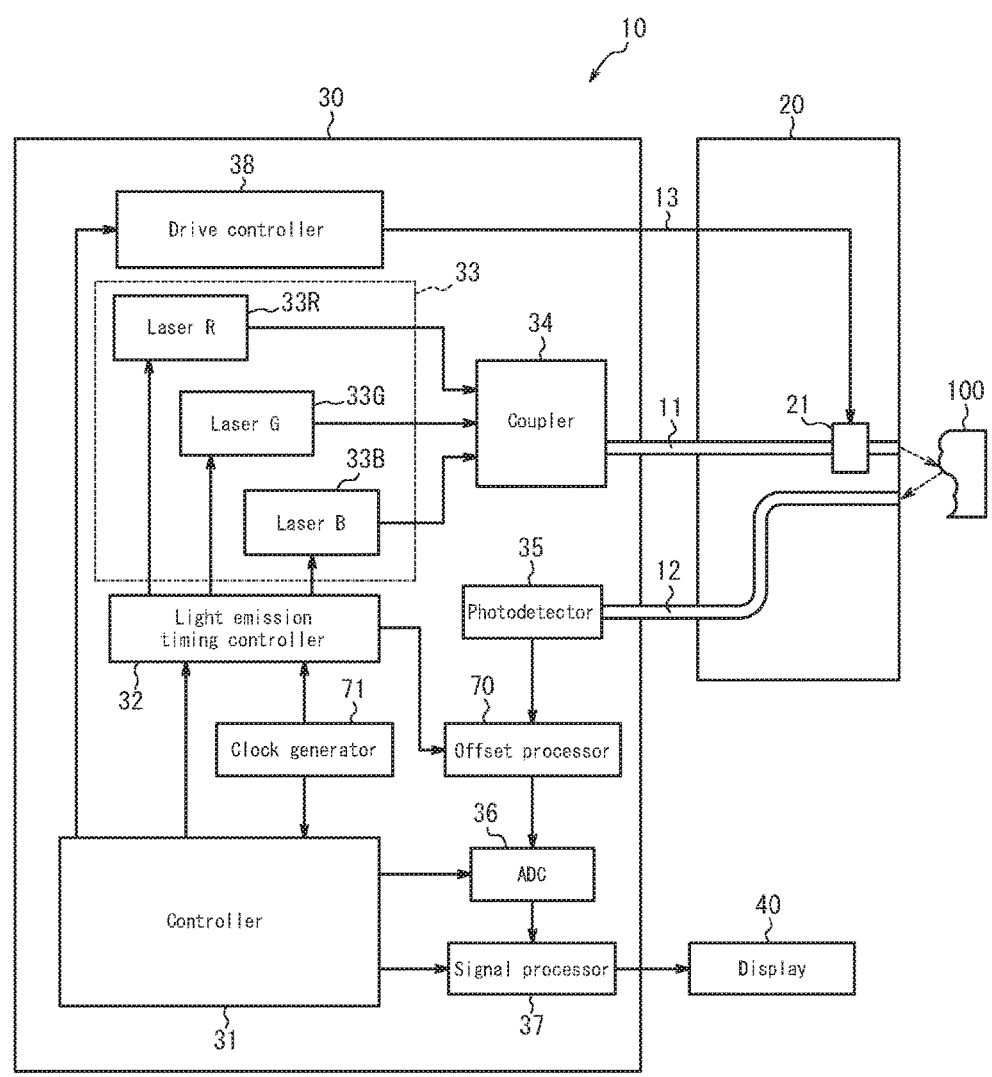
FIG. 1 is a block diagram schematically illustrating the structure of an optical scanning endoscope apparatus that is an example of an optical scanning observation apparatus according to Embodiment b.

With reference to FIGS. 1 to 9, Embodiment 1 is described. FIG. 1 is a block diagram schematically illustrating the structure of an optical scanning endoscope apparatus that is an example of an optical scanning observation apparatus according to Embodiment 1. In FIG. 1, an optical scanning endoscope apparatus 10 includes a scope 20, a control device body 30, and a display 40.

First, the structure of the control device body 30 is described. The control device body 30 includes a controller 31 that controls the optical scanning endoscope apparatus 10 overall, a clock generator 71, a light emission timing controller 32, lasers 33R, 33G, and 33B, a coupler 34, a drive controller 38, a photodetector 35, an offset processor 70, an analog/digital converter (ADC) 36, and a signal processor 37.

The control device body 30 is a computer including a central processing unit (CPU), a main storage device such as RAM (Random Access Memory), and an auxiliary storage device. The auxiliary storage device is a non-transitory computer-readable storage medium such as an optical disc or a magnetic disk, and stores an image processing program. The CPU loads the image processing program stored in the auxiliary storage device into the main storage device, and then executes the program, thereby to implement the functions of the controller 31, the light emission timing controller 32, the signal processor 37, and the offset processor 70. Alternatively, the functions of the controller 31, the light emission timing controller 32, the signal processor 37, and the offset processor 70 may be implemented by dedicated hardware such as ASIC (Application Specific Integrated Circuit). Alternatively, the controller 31, the light emission timing controller 32, the signal processor 37, and the offset processor 70 may be embodied by one or more FPGA (Field-Programmable Gate Array) or one or more PLD (Programmable Logic Device).

The timing for correcting (also referred to below as "offset correction") the offset value due to dark current (black level) of the electrical signal output from the photodetector 35 is stored in advance in a memory (not illustrated) that is readable and writable by the controller 31. As described below in detail, the offset correction timing may be provided during the scanning period (i.e. within the display period of the image) or outside the scanning period (i.e. outside the display period of the image).

In accordance with a control signal from the controller 31, the light emission timing controller 32 controls the light emission timing of the lasers 33R, 33G, and 33B that respectively emit red (R), green (G), and blue (B) laser illumination light. The light emission timing is set so that during the scanning period excluding the offset correction timing, illumination light of each color is emitted sequentially at constant time intervals (light emission cycle $T_E$), and so that at the offset correction timing, light emission of all colors is suspended for a predetermined time $T_C$. Outside the scanning period, light emission of all colors is fundamentally suspended.

The lasers 33R, 33G, and 33B constitute a light source 33 that selectively emits illumination light of a plurality of different colors (in this embodiment, three colors: R, G, and B). As used herein, "selectively emits illumination light of a plurality of different colors" refers to illumination light of one color selected by the light emission timing controller 32 being emitted at a timing selected by the light emission timing controller 32. For example, Diode-Pumped Solid-State (DPSS) lasers or laser diodes may be used as the lasers 33R, 33G, and 33B.

In this disclosure, the "light emission cycle $T_E$" does not refer to the light emission cycle of each of the lasers 33R, 33G, and 33B constituting the light source 33, but rather to the light emission cycle of illumination light that is sequentially emitted from the light source 33.

The laser illumination light emitted from the lasers 33R, 33G, and 33B passes through optical paths joined coaxially by the coupler 34 and is incident as illumination light on an optical fiber 11 for illumination (fiber) that is a single-mode fiber. The coupler 34 may, for example, be configured using a dichroic prism or the like.

The lasers 33R, 33G, and 33B and the coupler 34 may be stored in a housing that is separate from the control device body 30 and is joined to the control device body 30 by a signal wire.

Illumination light incident on the optical fiber 11 for illumination from the coupler 34 is guided to the tip of the scope 20 and irradiated towards an object 100. At this time, by driving the driver 21 of the scope 20 by vibration, the drive controller 38 of the control device body 30 drives the tip of the optical fiber 11 for illumination by vibration. As a result, the illumination light emitted from the optical fiber 11 for illumination scans the observation surface of the object 100 in 2D, for example in a spiral shape. Detection light such as reflected light or scattered light that is obtained from the object 100 due to irradiation with the illumination light is received at the tip of an optical fiber bundle 12 for detection, which is constituted by multi-mode fibers, and is guided through the scope 20 to the control device body 30.

In this embodiment, the "scanning period" refers to the period over which illumination light emitted from the optical fiber 11 for illumination is used for 2D scanning of the observation surface of the object 100.

In each light emission cycle $T_E$ of the light source 33, the photodetector 35 detects detection light obtained via the optical fiber bundle 12 for detection from the object 100 due to irradiation by illumination light of one of the colors R, G, and B and outputs an analog signal (electrical signal) limited to the bandwidth of the color.

When the light emission timing controller 32 suspends light emission of the light source 33, the offset processor 70 corrects the offset value (black level) based on an electrical signal output from the photodetector 35 due to dark current. In greater detail, upon being notified by the light emission timing controller 32 that the offset correction timing has been reached, the offset processor 70 corrects the offset value. The time during which light emission is suspended at the offset correction timing (also referred to below as the "predetermined time at the offset correction timing") $T_C$ is set in advance to be at least the length of time necessary to correct the offset value. The offset processor 70 corrects the offset value for example by clamping the electrical signal from the photodetector 35 and setting the black level of the electrical signal to a predetermined voltage. Once an electrical signal is output from the photodetector 35 after the offset correction timing, the offset processor 70 outputs the electrical signal with the corrected offset value to the ADC 36.

The ADC 36 converts the analog signal with the corrected offset value, which was input from the photodetector 35 via the offset processor 70, to a digital signal (electrical signal) and outputs the result to the signal processor 37.

The signal processor 37 associates the digital signals having corrected offset values, which were input from the ADC 36 at each light emission cycle $T_E$, with the respective light emission timings and scanning positions, and stores the results sequentially in memory (not illustrated). Information on the light emission timing and scanning position is acquired from the controller 31. The controller 31 calculates information on the scanning position along the scanning path from information such as the amplitude and phase of vibration voltage applied by the drive controller 38. After completion of scanning or during the scanning period, the signal processor 37 generates an image signal by performing necessary image processing, such as enhancement, y processing, and interpolation, based on each digital signal input from the ADC 36 and displays an image of the object 100 on the display 40.

The clock generator 71 is connected to the controller 31 and the light emission timing controller 32 and outputs a reference clock signal to the controller 31 and the light emission timing controller 32. The controller 31 divides the clock signal from the clock generator 71 to generate the control timing of the driver 21 by the drive controller 38 and the sampling timing by the ADC 36. On the other hand, the light emission timing controller 32 divides the clock signal from the clock generator 71 to generate the light emission timing of the lasers 33R, 33G, and 33B and the offset value correction timing of the offset processor 70. In this way, by causing the light emission timing controller 32, drive controller 38, and ADC 36 to operate based on the clock signal from the same clock generator 71, these operations can be reliably synchronized to allow reliable correction of the offset value without any misalignment in the timing.

Figure 2:
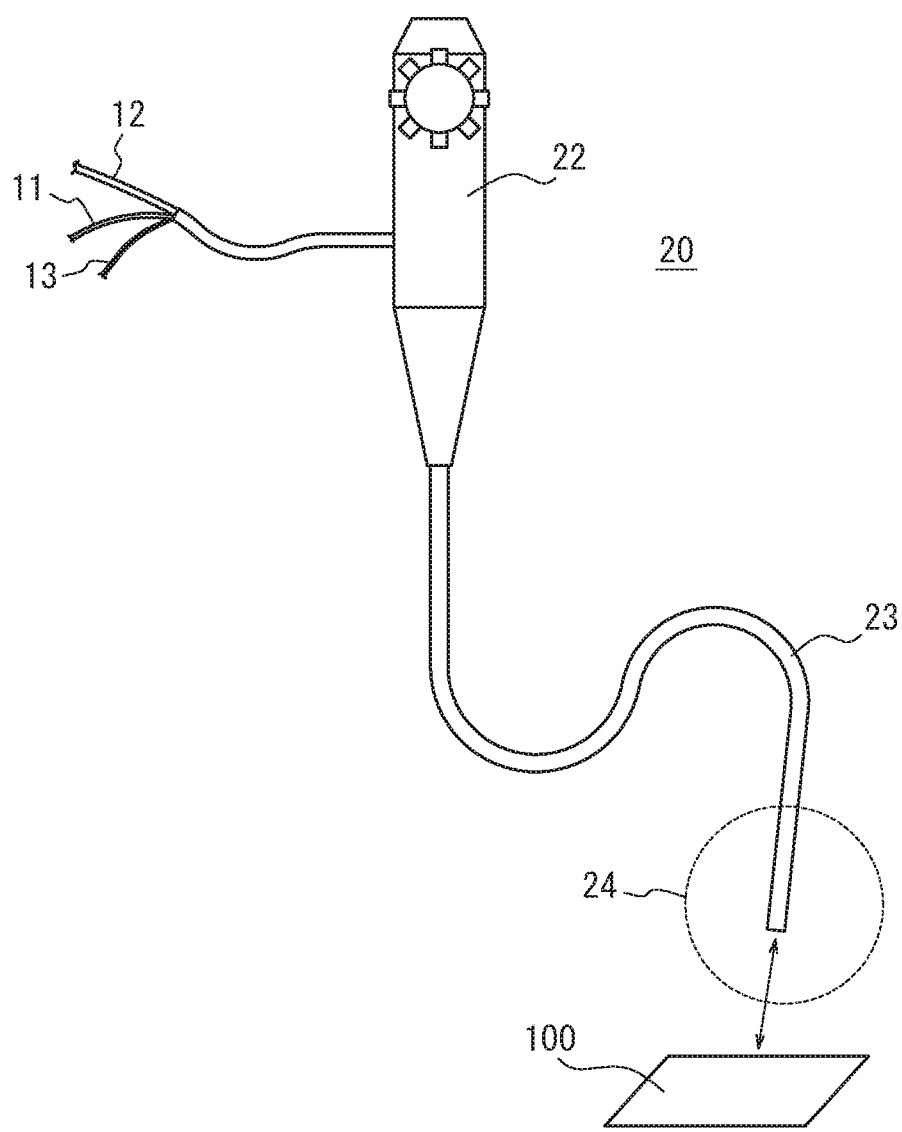
FIG. 2 is a schematic overview of the scope in FIG. 1.

Next, the structure of the scope 20 is described. FIG. 2 is a schematic overview of the scope 20. The scope 20 includes an operation part 22 and an insertion part 23. The optical fiber 11 for illumination, the optical fiber bundle 12 for detection, and a wiring cable 13 extending from the control device body 30 are each connected to the operation part 22. The optical fiber 11 for illumination, optical fiber bundle 12 for detection, and wiring cable 13 pass through the insertion part 23 and extend to a tip 24 (the portion within the dotted line in FIG. 2) of the insertion part 23.

Figure 3:
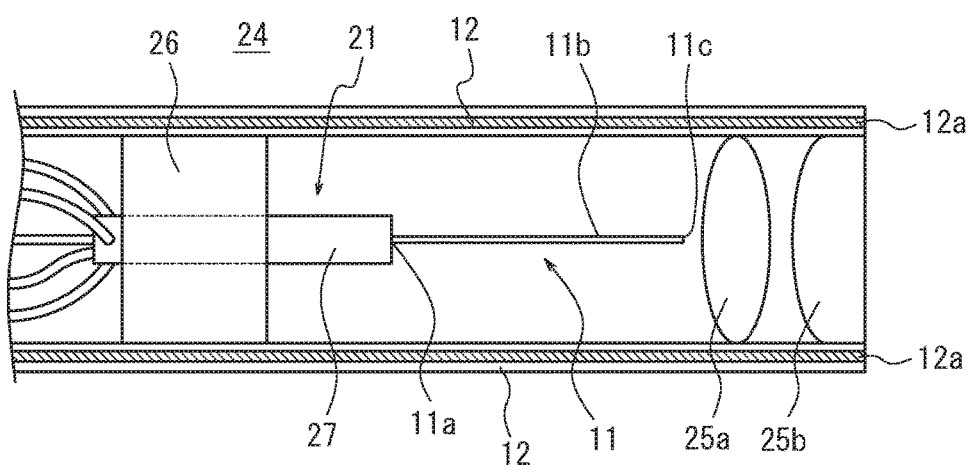
FIG. 3 is a cross-sectional diagram of the tip of the scope in FIG. 2.

FIG. 3 is a cross-sectional diagram illustrating an enlargement of the tip 24 of the insertion part 23 of the scope 20 in FIG. 2. The tip 24 of the insertion part 23 of the scope 20 includes the driver 21, projection lenses 25a and 25b (optical system), the optical fiber 11 for illumination that passes through the central portion, and the optical fiber bundle 12 for detection that passes through the peripheral portion.

The driver 21 drives a tip 11c of the optical fiber 11 for illumination by vibration. The driver 21 includes an actuator tube 27 fixed to the inside of the insertion part 23 of the scope 20 by an attachment ring 26, a fiber holding member 29 disposed inside the actuator tube 27, and piezoelectric elements 28a to 28d (see FIGS. 4A and 4B). The optical fiber 11 for illumination is supported by the fiber holding member 29, and the portion from a fixed end 11a supported by the fiber holding member 29 to the tip 11c is an oscillating part 11b that is supported to allow oscillation. The optical fiber bundle 12 for detection is disposed to pass through the peripheral portion of the insertion part 23 and extends to the end of the tip 24. A non-illustrated detection lens is also provided at the tip of each fiber in the optical fiber bundle 12 for detection.

Furthermore, the projection lenses 25a and 25b and the detection lenses are disposed at the extreme end of the tip 24 of the insertion part 23 in the scope 20. The projection lenses 25a and 25b are configured so that laser illumination light emitted from the tip 11c of the optical fiber 11 for illumination is irradiated on the object 100 and roughly concentrated. The detection lenses are disposed so that detection light that is reflected, scattered, refracted, or the like by the object 100 (detection light that interacted with the object 100) due to laser illumination light concentrated on the object 100 is captured, concentrated on the optical fiber bundle 12 for detection disposed behind the detection lenses, and combined. The detection lenses are not limited to a double lens structure and may be structured as a single lens or as three or more lenses.

Figure 4A:
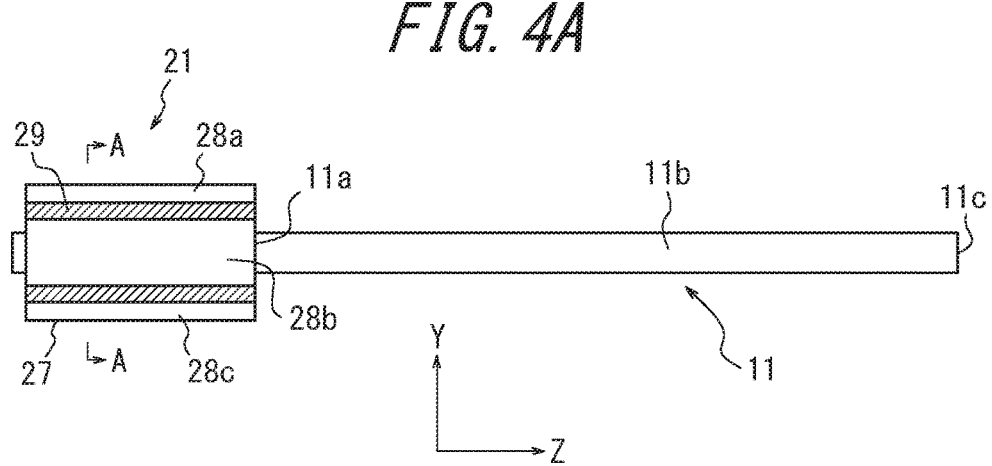
FIG. 4A is a side view.
Figure 4B:
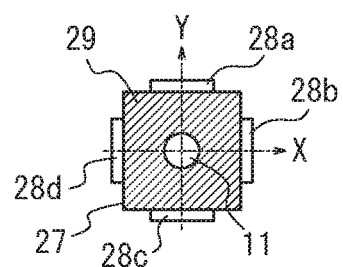
FIG. 4B is a cross-sectional diagram along the A-A line in FIG. 4A, illustrating the driver and the oscillating portion of the optical fiber for illumination in FIG. 3.

FIG. 4A illustrates the vibration driving mechanism of the driver 21 of the optical scanning endoscope apparatus 10 and illustrates the oscillating part 11b of the optical fiber 11 for illumination. FIG. 4B is a cross-sectional diagram along the A-A line in FIG. 4A. The optical fiber 11 for illumination passes through the center of the fiber holding member 29, which has a prismatic shape, and is fixed and held by the fiber holding member 29. The four sides of the fiber holding member 29 respectively face the ±Y direction and the ±X direction. A pair of piezoelectric elements 28a and 28c for driving in the Y direction are fixed onto the sides of the fiber holding member 29 in the ±Y direction, and a pair of piezoelectric elements 28b and 28d for driving in the X direction are fixed onto the sides in the ±X direction.

The wiring cable 13 from the drive controller 38 of the control device body 30 is connected to the piezoelectric elements 28a to 28d, which are driven by application of voltage by the drive controller 38.

Voltage of equivalent magnitude and opposite sign is always applied across the piezoelectric elements 28b and 28d in the X direction. Similarly, voltage of equivalent magnitude and opposite sign is always applied across the piezoelectric elements 28a and 28c in the Y direction. One of the piezoelectric elements 28b and 28d disposed opposite each other with the fiber holding member 29 therebetween expands and the other contracts, thereby causing the fiber holding member 29 to flex. Repeating this operation produces vibration in the X direction. The same is true for vibration in the Y direction as well.

The drive controller 38 can perform vibration driving of the piezoelectric elements 28b and 28d for driving in the X direction and the piezoelectric elements 28a and 28c for driving in the Y direction by applying vibration voltage of the same frequency or vibration voltage of different frequencies thereto. Upon vibration driving of the piezoelectric elements 28a and 28c for driving in the Y direction and the piezoelectric elements 28b and 28d for driving in the X direction, the oscillating part 11b of the optical fiber 11 for illumination illustrated in FIGS. 3, 4A, and 4B vibrates, and the tip 11c is deflected, so that the laser illumination light emitted from the tip 11c sequentially (for example, in a spiral shape) scans the surface of the object 100.

Next, the operation of the optical scanning endoscope apparatus 10 is described with reference to FIGS. 5A to 5G, focusing on processing by the light emission timing controller 32, offset processor 70, and signal processor 37. FIGS. 5A to 5G illustrate an example of the relationship between the light emission timing and the correction timing of the offset value. Time proceeds from the left to the right of the figures. In the example in FIGS. 5A to 5G, the offset correction timing is provided during the scanning period, specifically between predetermined pixels, with R, G, and B light emission constituting one pixel. FIGS. 5A to 5C illustrate the light emission timing of the lasers 33R, 33G, and 33B. FIG. 5D illustrates the output of the coupler 34. FIG. 5E illustrates the output of the photodetector 35. FIG. 5F illustrates pixels processed by the signal processor 37. FIG. 5G illustrates the timing of correction of the offset value by the offset processor 70.

During the scanning period excluding the offset correction timing, the light emission timing controller 32 controls the light emission timing of the lasers 33R, 33G, and 33B in the order of R, G, and B in each light emission cycle $T_E$ in accordance with a control signal from the controller 31.

During this time, an electrical signal corresponding to each color output from the photodetector 35 is output to the signal processor 37 via the offset processor 70 and the ADC 36.

Upon reaching the offset correction timing, the light emission timing controller 32 suspends emission of illumination light by all of the lasers 33R, 33G, and 33B for the entire predetermined time $T_C$. During this time, only the electrical signal due to dark current (offset value) is output from the photodetector 35. The offset processor 70 corrects the offset value based on the electrical signal output from the photodetector 35.

At the end of the offset correction timing that lasts throughout the predetermined time $T_C$, the light emission timing controller 32 once again controls the light emission timing of the lasers 33R, 33G, and 33B in the order of R, G, and B in each light emission cycle $T_E$. During this time, the electrical signal corresponding to each color output from the photodetector 35 is output to the ADC 36 with the offset value having been corrected by the offset processor 70 and is subsequently output to the signal processor 37.

As illustrated in FIG. 5F, the signal processor 37 generates image signals based on the R, G, and B electrical signals input sequentially from the photodetector 35 via the offset processor 70 and the ADC 36 and outputs the result to the display 40. At this time, the pixel that could not be acquired during the predetermined time $T_C$ at the offset correction timing is preferably interpolated from neighboring pixels with a known method, thereby preventing the portion corresponding to the predetermined time $T_C$ from appearing as a black spot within the image. Good image definition of the image can thus be achieved. The "neighboring pixels" referred to here are neighboring pixels along the scanning trajectory of the tip 11c of the optical fiber 11 for illumination or neighboring pixels present upon generation of the image signal output to the display 40.

Examples of the relationship between the scanning trajectory of the tip 11c of the optical fiber 11 for illumination and the offset correction timing are now described with reference to FIGS. 6 to 9. In the figures, the solid line t indicates the scanning trajectory of the tip 11c, whereas the points c represent the position of the tip 11c on the scanning trajectory t at the offset correction timing.

Figure 6:
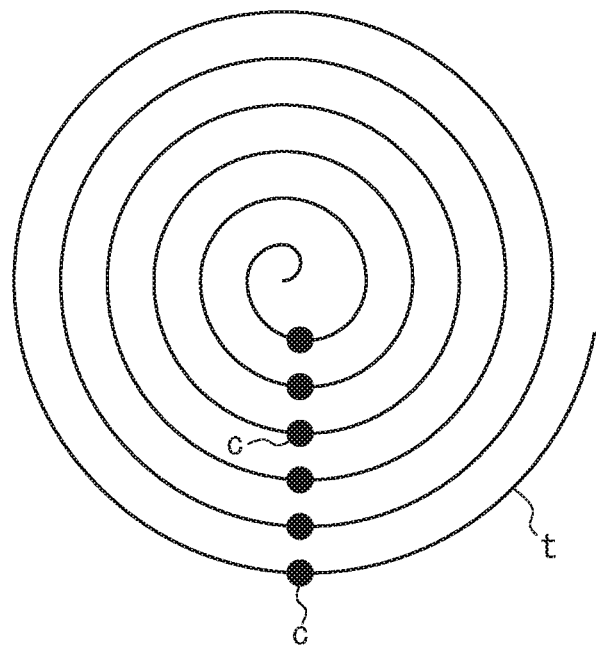
FIG. 6 illustrates a first example of the relationship between the scanning trajectory and the correction timing of the offset value.

The first example in FIG. 6 illustrates the case of the tip 11c of the optical fiber 11 for illumination oscillating in a spiral shape from the inner periphery towards the outer periphery due to the driver 21 during the scanning period. In this example, the offset correction timing is provided during the scanning period each time the tip 11c completes one scanning revolution. Therefore, the positions c of the tip 11c at each offset correction timing are aligned in a row that is vertical in the illustrated example. Accordingly, the portion at each point c at which the offset value is corrected can, for example, be interpolated based on neighboring pixels positioned on either side (to the left and right in the illustrated example) of the row of positions c along the scanning trajectory. By providing the offset correction timing during the scanning period, the black level of the image during the scanning period can be maintained constant, improving image quality.

Figure 7:
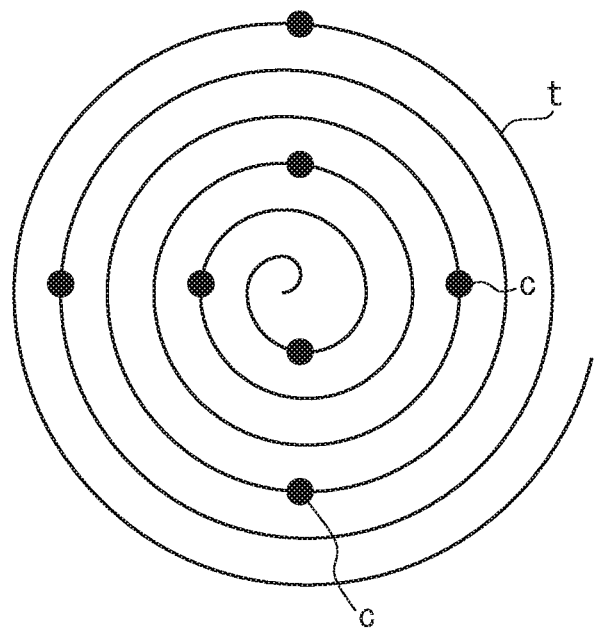
FIG. 7 illustrates a second example of the relationship between the scanning trajectory and the correction timing of the offset value.

The second example in FIG. 7 differs from the first example in that the offset correction timing is provided during the scanning period each time the tip 11c completes ¾ of a scanning revolution. Therefore, as compared to the first example, the positions c along the scanning trajectory t of the tip 11c at the offset correction timings are farther apart from each other. Accordingly, the pixel at each point c at which the offset value is corrected can, for example, be interpolated based on neighboring pixels that are vertically and horizontally adjacent to the positions c along the scanning trajectory. In this way, according to the second example, the portion at each position c can be interpolated based on a greater number of neighboring pixels than in the first example. Hence, in addition to the effects of the first example, the accuracy of interpolation can be improved, thereby improving the definition of the image.

Figure 8:
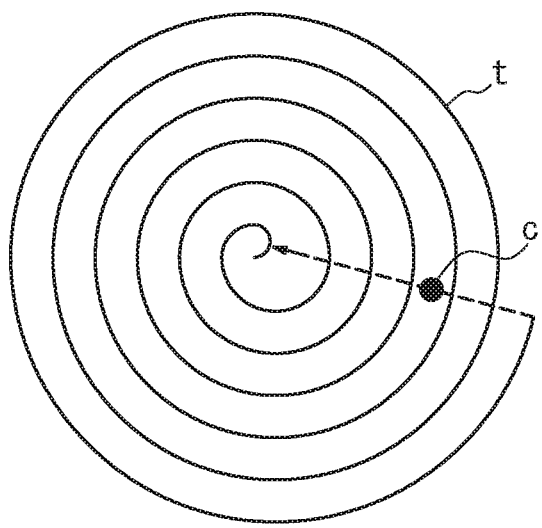
FIG. 8 illustrates a third example of the relationship between the scanning trajectory and the correction timing of the offset value.

In the third example illustrated in FIG. 8, the offset correction timing is provided outside the scanning period (outside the display period of the image) when the light source 33 is not emitting illumination light, during the period in which the tip 11c of the optical fiber 11 for illumination returns to the initial position after completion of scanning, for example in a spiral from the outer periphery towards the inner periphery ("return period"). By providing the offset correction timing during the return period, the quality of the image displayed during the next scan can be improved. Furthermore, since there is no portion in the image for which light emission of the light source 33 is suspended, it is not necessary to perform the interpolation processing that, in the case of providing the offset correction timing during the scanning period, is required for the pixel that cannot be acquired at the offset correction timing.

The offset correction timing may be provided at any timing during the scanning period other than the first and second examples. Also, the first, second, and third examples may for example be combined to provide the offset correction timing both during the scanning period and outside the scanning period.

Figure 9:
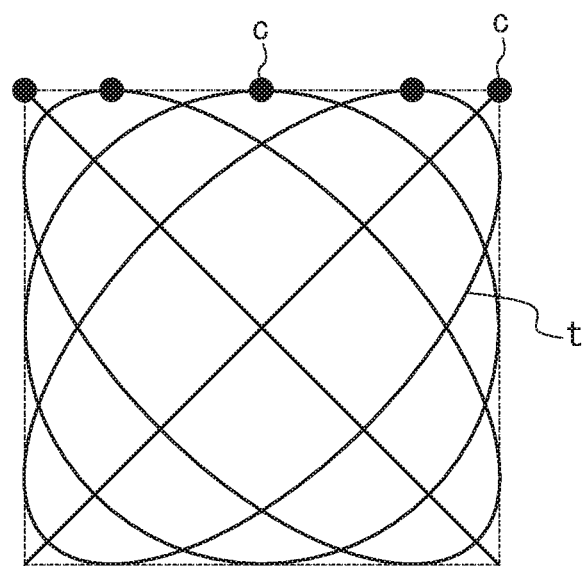
FIG. 9 illustrates a fourth example of the relationship between the scanning trajectory and the correction timing of the offset value.

The fourth example in FIG. 9 illustrates the case of the tip 11c of the optical fiber 11 for illumination being oscillated in a Lissajous curve by the driver 21 during the scanning period. The scanning trajectory of the Lissajous curve passes through the outer peripheral region of the image at least once per revolution. Here, "through the outer peripheral region of the image" refers to the region at the outer periphery of the image, excluding the central region. In this example, the offset correction timings are provided while the tip 11c of the optical fiber 11 for illumination passes through the outer peripheral region of the image (in greater detail, at the upper edge of the image). According to this example, as in the first and second examples, the black level of the image during the scanning period can be maintained constant by providing the offset correction timing during the scanning period, thereby improving image quality.

Furthermore, since there is no portion in the central region of the image for which light emission of the light source 33 is suspended, sufficiently good image quality can be obtained even without interpolating the pixels that cannot be acquired at the offset correction timings. Furthermore, by using the scanning trajectory in a Lissajous curve, the return period that is required when using a scanning trajectory in a spiral shape is unnecessary, allowing continuous scanning to be maintained. Hence, the offset value can be corrected frequently, which is particularly advantageous when the variation in the offset value is intense.

Any trajectory other than the trajectory in a spiral shape and a

Lissajous curve described in the first to fourth examples may also be used in this disclosure.

According to Embodiment 1, even when the offset value of the electrical signal output from the photodetector 35 varies due to the usage environment, such as the temperature, the black level of the image is maintained constant by correcting the offset value. The image quality can thus be improved.

Embodiment 2

Figure 10:
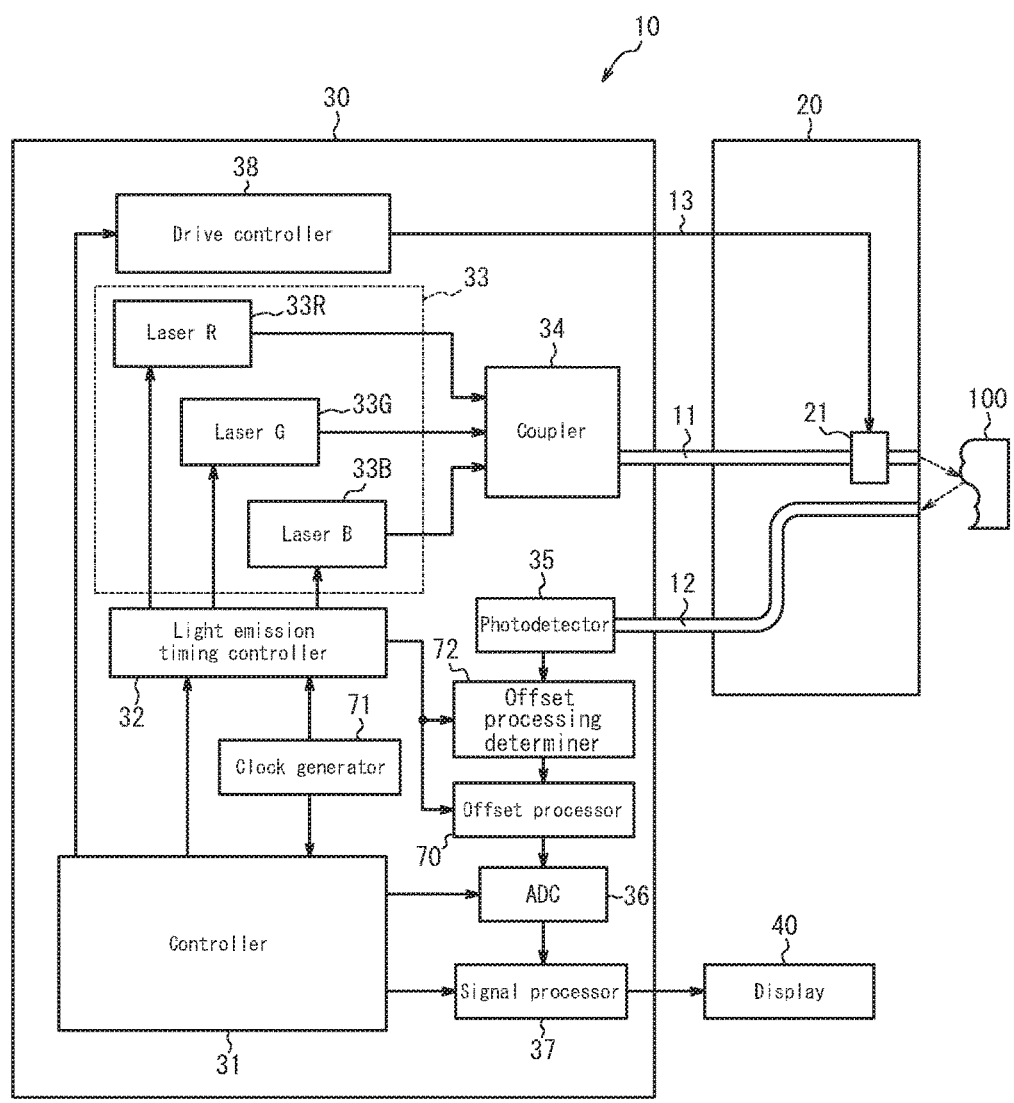
FIG. 10 is a block diagram schematically illustrating the structure of an optical scanning endoscope apparatus that is an example of an optical scanning observation apparatus according to Embodiment 2.
Figure 11:
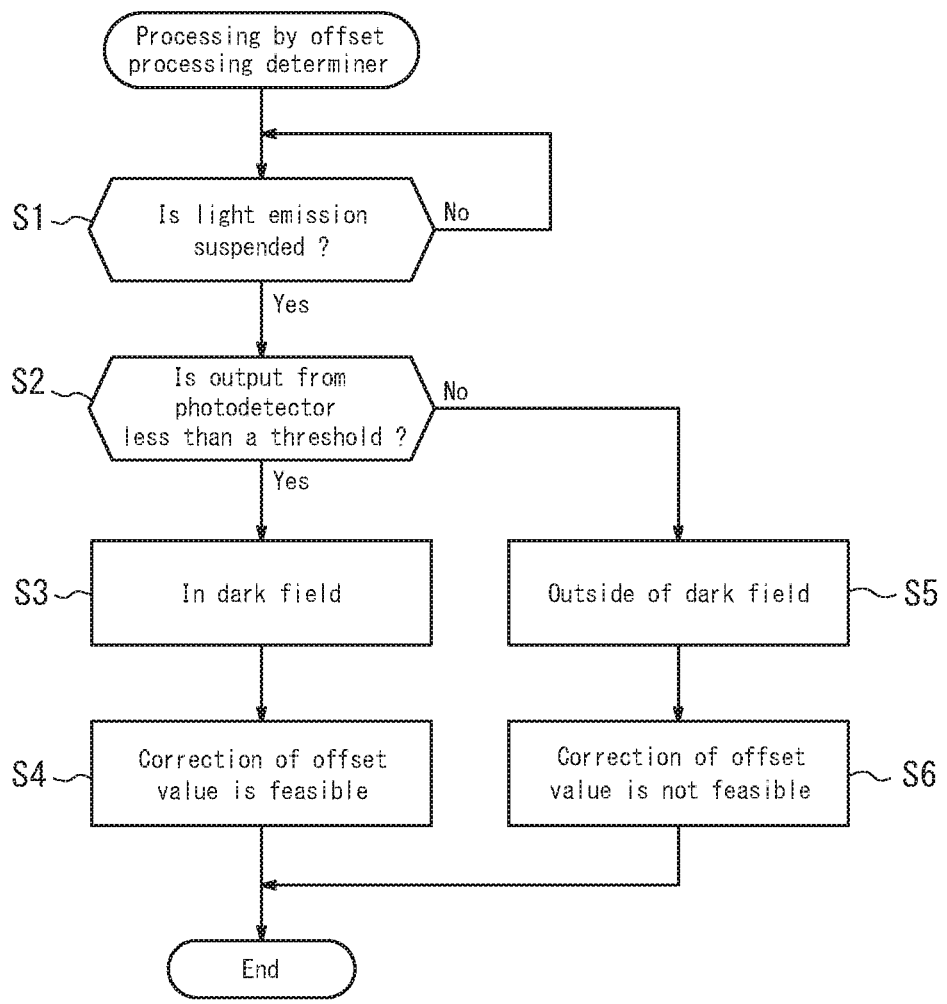
FIG. 11 is a flowchart illustrating processing by the offset processing determiner in FIG. 10.

With reference to FIGS. 10 to 11, Embodiment 2 is described. FIG. 10 is a block diagram schematically illustrating the structure of an optical scanning endoscope apparatus that is an example of an optical scanning observation apparatus according to Embodiment 2. This embodiment only differs from Embodiment 1 in that the control device body 30 further includes an offset processing determiner 72. Therefore, a description of the remaining structure is omitted.

The control device body 30 is a computer including a central processing unit (CPU), a main storage device such as RAM (Random Access Memory), and an auxiliary storage device. The auxiliary storage device is a non-transitory computer-readable storage medium such as an optical disc or a magnetic disk, and stores an image processing program. The CPU loads the image processing program stored in the auxiliary storage device into the main storage device, and then executes the program, thereby to implement the functions of the controller 31, the light emission timing controller 32, the signal processor 37, the offset processor 70, and the offset processing determiner 72. Alternatively, the functions of the controller 31, the light emission timing controller 32, the signal processor 37 the offset processor 70, and the offset processing determiner 72 may be implemented by dedicated hardware such as ASIC (Application Specific Integrated Circuit). Alternatively, the controller 31, the light emission timing controller 32, the signal processor 37, the offset processor 70, and the offset processing determiner 72 may be embodied by one or more FPGA (Field-Programmable Gate Array) or one or more PLD (Programmable Logic Device).

In Embodiment 1, the offset value is corrected when light emission of the light source 33 is suspended. Even if light emission of the light source 33 is suspended, however, a detected value of external light also ends up being output in addition to the offset value due to dark current from the photodetector 35 when the tip 24 of the insertion part 23 of the scope 20 is outside of a dark field, such as being outside of a patient's body. In this case, the offset value cannot be accurately corrected. To address this issue, the offset value is not corrected in this embodiment when the tip 24 of the insertion part 23 of the scope 20 is outside of a dark field, thereby avoiding inaccurate correction of the offset value.

As illustrated in FIG. 10, the offset processing determiner 72 is connected to the photodetector 35, the offset processor 70, and the light emission timing controller 32. Based on the electrical signal output from the photodetector 35 when the light emission timing controller 32 has suspended light emission of the light source 33, the offset processing determiner 72 determines whether correction of the offset value is feasible and notifies the offset processor 70 of the determination result. When the offset processing determiner 72 determines that correction of the offset value is feasible, the offset processor 70 corrects the offset value as described in Embodiment 1.

Next, the operation of the optical scanning endoscope apparatus 10 is described with reference to FIG. 11, focusing on processing by the offset processing determiner 72. FIG. 11 is a flowchart illustrating processing by the offset processing determiner 72. First, based on notification from the light emission timing controller 32, the offset processing determiner 72 determines whether the light emission timing controller 32 has suspended light emission of the light source 33 (step S1). Here, the time during which light emission of the light source 33 is suspended is the predetermined time $T_C$ at the offset correction timing during the scanning period or is a time outside the scanning period.

Upon determining that the light emission timing controller 32 has suspended light emission of the light source 33 (step S1: Yes), the offset processing determiner 72 determines whether the value of the electrical signal output from the photodetector 35 is less than a predetermined threshold (step S2). This threshold is preferably set to the minimum output value that is envisioned as being output from the photodetector 35 when the tip 24 of the insertion part 23 of the scope 20 is outside of a dark field (such as being outside of a patient's body). The threshold may be changed, however, in accordance with the environment in which the optical scanning endoscope apparatus 10 is used.

When the value of the electrical signal output from the photodetector 35 is less than the threshold (step S2: Yes), the offset processing determiner 72 determines that the tip 24 of the insertion part 23 of the scope 20 is in a dark field (step S3), determines that correction of the offset value is feasible (step S4), and notifies the offset processor 70 of the determination result. After receiving this notification, the offset processor 70 corrects the offset value as described in Embodiment 1 at the offset correction timing.

Conversely, when the value of the electrical signal output from the photodetector 35 is equal to or greater than the threshold in step S2 (step S2: No), the offset processing determiner 72 determines that the tip 24 of the insertion part 23 of the scope 20 is outside of a dark field (step S5), determines that correction of the offset value is not feasible (step S6), and notifies the offset processor 70 of the determination result. After receiving this notification, the offset processor 70 does not correct the offset value even when reaching the offset correction timing. In this case, the electrical signal output from the photodetector 35 is output to the ADC 36 with the offset value in an uncorrected state.

According to Embodiment 2, in addition to the effects of Embodiment 1, the offset value is not corrected when the tip 24 of the insertion part 23 of the scope 20 is outside of a dark field, thereby avoiding inaccurate correction of the offset value.

Instead of step S1 in FIG. 11, the offset processing determiner 72 may proceed to step S2 when determining that the current time is within the predetermined time $T_C$ at the offset correction timing based on notification from the light emission timing controller 32.

Instead of step S2 in FIG. 11, or in addition to step S2, the offset processing determiner 72 may proceed to step S3 when determining that the waveform of the electrical signal output from the photodetector 35 during the light emission period of the light source 33 immediately before light emission of the light source 33 is suspended has a pulse shape, i.e. when determining that an object is being scanned. Stating that "the waveform has a pulse shape" refers to the output waveform from the photodetector 35 not being an approximately flat shape but rather having a peak each time the colors of R, G, and B are detected, as illustrated in FIG. 5E. In this case, means for sampling the output signal from the photodetector 35 over an immediately previous predetermined time at predetermined time intervals needs to be provided separately. Based on data of the output signal sampled by this means, the offset processing determiner 72 determines whether the output waveform of the photodetector 35 has a pulse shape.

In Embodiments 1 and 2, the structure of the offset processor 70 is not limited to correcting the offset value in an analog signal state and may instead correct the offset value after conversion to a digital signal. For example, the offset processor 70 may correct the offset value by converting to analog the offset value that has been converted from analog to digital by the ADC 36 and then performing feedback control so that the converted offset value becomes a constant value. Alternatively, the offset processor 70 may be connected to the output side of the ADC 36 and may correct the offset value that has been converted from analog to digital by the ADC 36 so that the offset value matches the black level of the image.

In Embodiments 1 and 2, the drive controller 38 may be provided internally with a different clock generator than the clock generator 71 used by the controller 31 and may be configured to operate based on a clock signal from this internal clock generator. In this case, as compared to when the controller 31 and the drive controller 38 share use of the clock generator 71, the power consumption can be reduced by the amount of power that would have been required for distributing the clock signal to the drive controller 38.

In Embodiments 1 and 2, the light source 33 of the optical scanning endoscope apparatus 10 is not limited to being configured with the lasers 33R, 33G, and 33B. For example, a white light source 33 that emits pulsed illumination light may be provided.

Figure 12A:
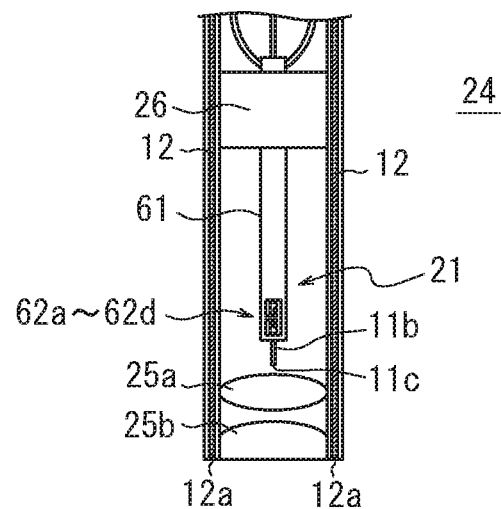
FIGS. 12A to 12C illustrate modifications to the driver in FIG. 4, where
Figure 12B:
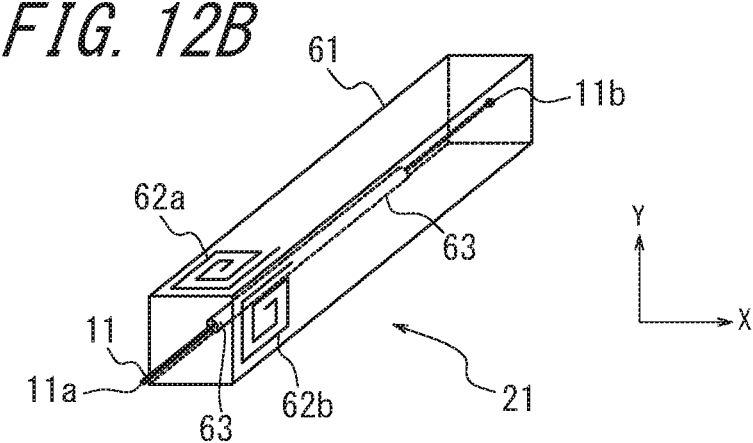
Figure 12C:
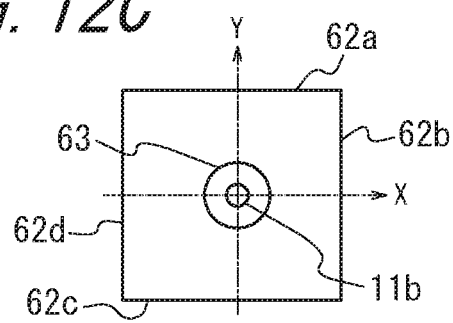

Furthermore, in Embodiments 1 and 2, the driver 21 of the optical fiber 11 for illumination is not limited to use of piezoelectric elements. For example, a permanent magnet fixed to the optical fiber 11 for illumination and coils for generation of a deflecting magnetic field (magnet coils) that drive the permanent magnet may be used instead. The following describes a modification to the driver 21 with reference to FIGS. 12A to 12C. FIG. 12A is a cross-sectional diagram of the tip 24 of the scope 20, FIG. 12B is an enlarged perspective view of the driver 21 in FIG. 12A, and FIG. 12C is a cross-sectional view along a plane perpendicular to the axis of the optical fiber 11 for illumination, illustrating a portion including the coils 62a to 62d for generation of a deflecting magnetic field and the permanent magnet 63 in FIG. 12B.

At a portion of the oscillating part 11b of the optical fiber 11 for illumination, the permanent magnet 63, which is magnetized in the axial direction of the optical fiber 11 for illumination and includes a through-hole, is joined to the optical fiber 11 for illumination by the optical fiber 11 being passed through the through-hole. A square tube 61, one end of which is fixed to the attachment ring 26, is provided so as to surround the oscillating part 11b, and flat coils 62a to 62d for generation of a deflecting magnetic field are provided on the sides of the square tube 61 at a portion thereof opposing one pole of the permanent magnet 63.

The pair of coils 62a and 62c for generation of a deflecting magnetic field in the Y direction and the pair of coils 62b and 62d for generation of a deflecting magnetic field in the X direction are each disposed on opposing sides of the square tube 61, and a line connecting the center of the coil 62a for generation of a deflecting magnetic field with the center of the coil 62c for generation of a deflecting magnetic field is orthogonal to a line connecting the center of the coil 62b for generation of a deflecting magnetic field with the center of the coil 62d for generation of a deflecting magnetic field near the central axis of the square tube 61 when the optical fiber 11 for illumination is disposed therein at rest. These coils are connected to the drive controller 38 of the control device body 30 via the wiring cable 13 and are driven by drive current from the drive controller 38.

The optical scanning observation apparatus of this disclosure can be applied not only to an optical scanning endoscope apparatus, but also to another optical scanning observation apparatus such as an optical scanning microscope.

The invention claimed is:

1. An optical scanning observation apparatus for scanning an object with illumination light from a light source and acquiring an image of the object, the optical scanning observation apparatus comprising:
   a light emission timing controller configured to control a light emission timing of the light source;
   a fiber configured to guide the illumination light from the light source and emit the illumination light toward the object from a tip of the fiber, the tip being supported to allow oscillation;
   a driver configured to drive the tip of the fiber by vibration;
   a photodetector configured to detect detection light obtained from the object and convert the detection light obtained from the object to an electrical signal;
   an offset processor configured to, in response to a notification that that light emission from the light source is suspended, correct an offset value among the electrical signal based on the electrical signal outputted by the photodetector; and
   a signal processor configured to generate an image signal based on the electrical signal with the corrected offset value.

2. The optical scanning observation apparatus of claim 1, wherein the driver oscillates the tip of the fiber in a spiral shape.

3. The optical scanning observation apparatus of claim 1, wherein the driver oscillates the tip of the fiber in a Lissajous curve.

4. The optical scanning observation apparatus of claim 1, wherein the light emission timing controller is further configured to suspend light emission of the light source, and the offset processor is further configured to correct the offset value, in an outer peripheral region of an image generated based on the image signal or outside a display period of the image.

5. The optical scanning observation apparatus of claim 1, further comprising:
   an offset processing determiner configured to determine whether correction of the offset value is feasible based on the electrical signal output by the photodetector while the light emission timing controller suspends light emission of the light source;
   wherein the offset processor corrects the offset value when the offset processing determiner determines that correction of the offset value is feasible.

6. The optical scanning observation apparatus of claim 1, wherein the signal processor is further configured to interpolate a pixel that could not be acquired during the suspension of the light emission of the light source from neighboring pixels of the pixel.

7. The optical scanning observation apparatus of claim 1, wherein the offset processor is further configured to determine that the correction of the offset value is feasible based on one or more of: a value of the electrical signal output and a waveform of the electrical signal output.

8. The optical scanning observation apparatus of claim 1, wherein the illumination light is pulsed illumination light, and the offset processor is further configured to determine that the correction of the offset value is feasible when a waveform of the electrical signal output includes a pulse shape.

\* \* \* \* \*